(12) United States Patent
Bor et al.

(10) Patent No.: US 9,101,446 B2
(45) Date of Patent: *Aug. 11, 2015

(54) SYSTEM AND METHOD FOR SCANNING A PULSED LASER BEAM

(71) Applicant: AMO Development, LLC., Santa Ana, CA (US)

(72) Inventors: Zsolt Bor, San Clemente, CA (US); Ruben Zadoyan, Irvine, CA (US); Marcel Bouvier, Aliso Viejo, CA (US); Guy V Holland, San Clemente, CA (US)

(73) Assignee: IntraLase Corp., Santa Ana, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 13/792,758

(22) Filed: Mar. 11, 2013

(65) Prior Publication Data

US 2013/0211390 A1  Aug. 15, 2013

Related U.S. Application Data

(63) Continuation-in-part of application No. 11/968,589, filed on Jan. 2, 2008.

(51) Int. Cl.
*A61F 9/008* (2006.01)
*B23K 26/08* (2014.01)
(Continued)

(52) U.S. Cl.
CPC .............. *A61F 9/008* (2013.01); *A61F 9/00829* (2013.01); *A61F 9/00836* (2013.01);
(Continued)

(58) Field of Classification Search
CPC ........................ A61F 2009/00872; A61F 9/008
USPC ......................................................... 606/4, 5
See application file for complete search history.

(56) References Cited

U.S. PATENT DOCUMENTS

| 4,764,930 A | 8/1988 | Bille et al. |
| 4,901,718 A | 2/1990 | Bille et al. |

(Continued)

FOREIGN PATENT DOCUMENTS

| DE | 102005039833 A1 | 3/2007 |
| EP | 1473006 A1 | 11/2004 |

(Continued)

OTHER PUBLICATIONS

International Preliminary Report on Patentability and Written Opinion for Application No. PCT/US08/088019, mailed on Jul. 6, 2010, 10 pages.

(Continued)

*Primary Examiner* — William Thomson
*Assistant Examiner* — Jeffrey Lipitz

(57) ABSTRACT

Systems and methods of photoaltering a region of a material using a pulsed laser beam. The method includes scanning the pulsed laser beam in a first portion of the region with a first pattern, scanning the pulsed laser beam in a second portion of the region with a second pattern, and separating a flap of the material at the region. The system includes a laser, a controller selecting at least first and second patterns, and a scanner operable in response to the controller. The first pattern has a first maximum acceleration associated with the second portion, and the second pattern has a second maximum acceleration associated with the second portion. The second maximum acceleration is less than the first maximum acceleration. The scanner scans the pulsed laser beam from the laser in the first portion with the first pattern and in the second portion with the second pattern.

18 Claims, 13 Drawing Sheets

(51) Int. Cl.
   *B23K 26/00* (2014.01)
   *B23K 26/06* (2014.01)
   *A61B 18/20* (2006.01)

(52) U.S. Cl.
   CPC ......... *B23K26/0084* (2013.01); *B23K 26/0635* (2013.01); *B23K 26/08* (2013.01); *B23K 26/0807* (2013.01); *A61B 2018/2085* (2013.01); *A61F 2009/0087* (2013.01); *A61F 2009/0088* (2013.01); *A61F 2009/00846* (2013.01); *A61F 2009/00872* (2013.01); *A61F 2009/00882* (2013.01); *A61F 2009/00897* (2013.01)

(56) References Cited

U.S. PATENT DOCUMENTS

| | | |
|---|---|---|
| 4,907,586 A | 3/1990 | Bille et al. |
| 5,520,679 A | 5/1996 | Lin |
| 5,549,632 A | 8/1996 | Lai |
| 5,599,340 A | 2/1997 | Simon et al. |
| 5,656,186 A | 8/1997 | Mourou et al. |
| 5,800,424 A | 9/1998 | Sumiya |
| 5,993,438 A | 11/1999 | Juhasz et al. |
| 6,090,100 A | 7/2000 | Hohla |
| 6,110,166 A | 8/2000 | Juhasz |
| 6,203,539 B1 | 3/2001 | Shimmick et al. |
| 6,325,792 B1 | 12/2001 | Swinger et al. |
| RE37,585 E | 3/2002 | Mourou et al. |
| 6,451,006 B1 | 9/2002 | Bille |
| 6,454,411 B1 | 9/2002 | Trumbull |
| 6,610,050 B2 | 8/2003 | Bille |
| 6,641,577 B2 | 11/2003 | Bille |
| 6,676,653 B2 | 1/2004 | Juhasz et al. |
| 6,751,033 B2 | 6/2004 | Goldstein et al. |
| 7,027,233 B2 | 4/2006 | Goldstein et al. |
| 7,131,968 B2 | 11/2006 | Bendett et al. |
| 2001/0010003 A1 | 7/2001 | Lai |
| 2001/0016736 A1 | 8/2001 | Lin |
| 2001/0037105 A1 | 11/2001 | Lin |
| 2002/0111607 A1 | 8/2002 | Bille |
| 2003/0132208 A1 | 7/2003 | Cutler |
| 2003/0208189 A1 | 11/2003 | Payman |
| 2003/0212387 A1 | 11/2003 | Kurtz et al. |
| 2003/0229339 A1 | 12/2003 | Bille |
| 2004/0199150 A1 | 10/2004 | Lai |
| 2004/0209410 A1 | 10/2004 | Tanaka |
| 2004/0243111 A1* | 12/2004 | Bendett et al. ............ 606/5 |
| 2004/0243112 A1* | 12/2004 | Bendett et al. ............ 606/5 |
| 2005/0149006 A1 | 7/2005 | Peyman |
| 2005/0228366 A1 | 10/2005 | Kessler et al. |
| 2005/0245915 A1 | 11/2005 | Loesel et al. |
| 2006/0027544 A1* | 2/2006 | Pailthorp et al. ......... 219/121.71 |
| 2006/0095024 A1 | 5/2006 | Dippolito |
| 2006/0155265 A1 | 7/2006 | Juhasz et al. |
| 2006/0195076 A1 | 8/2006 | Blumenkranz et al. |
| 2007/0055221 A1 | 3/2007 | Lubatschowski et al. |
| 2007/0078447 A1 | 4/2007 | Weinacht et al. |
| 2007/0088409 A1 | 4/2007 | Bischoff et al. |
| 2007/0179479 A1 | 8/2007 | Bille |
| 2007/0185475 A1 | 8/2007 | Frey et al. |
| 2007/0235543 A1 | 10/2007 | Zadoyan et al. |
| 2008/0051769 A1 | 2/2008 | Mrochen et al. |
| 2009/0118716 A1 | 5/2009 | Brownell |
| 2009/0118718 A1 | 5/2009 | Raksi et al. |
| 2009/0126870 A1 | 5/2009 | Zadoyan et al. |
| 2009/0157061 A1* | 6/2009 | Ruiz et al. ............ 606/5 |

FOREIGN PATENT DOCUMENTS

| | | |
|---|---|---|
| EP | 1591087 A1 | 11/2005 |
| EP | 1731120 A1 | 12/2006 |
| EP | 1834615 A1 | 9/2007 |
| WO | 9717903 A1 | 5/1997 |
| WO | 2004003625 A1 | 1/2004 |
| WO | 2004017878 A1 | 3/2004 |
| WO | 2005058216 A1 | 6/2005 |

OTHER PUBLICATIONS

International Search Report for Application No. PCT/US08/088019, mailed on Mar. 27, 2009, 4 pages.
Heisterkamp A., et al., "Optimizing Laser Parameters for Intrastromal Incision with Ultra-Short Laser Pulses," Ophthalmologe, 2001, vol. 98 (7), pp. 623-628.
International Preliminary Report on Patentability and Written Opinion for Application No. PCT/US08/082712, mailed on May 11, 2010, 8 pages.
International Preliminary Report on Patentability and Written Opinion for Application No. PCT/US08/084075, mailed on May 25, 2010, 8 pages.
International Search Report for Application No. PCT/US08/082712, mailed on Mar. 27, 2009, 4 pages.
International Search Report for Application No. PCT/US08/084075, mailed on Mar. 30, 2009, 4 pages.
International Search Report for Application No. PCT/US2014/020117, mailed on Jun. 17, 2014, 4 pages.

* cited by examiner

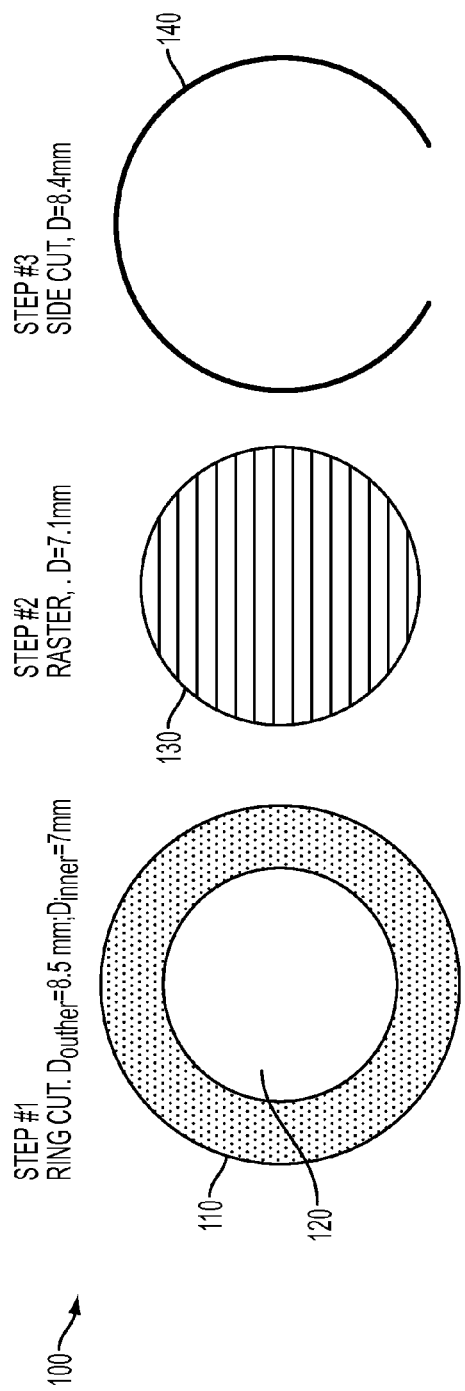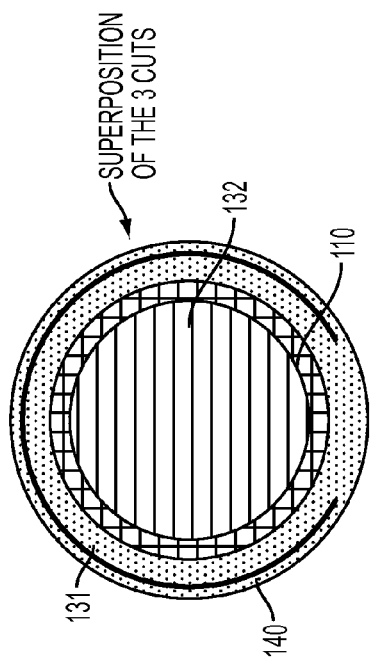

SYSTEM AND METHOD FOR SCANNING A PULSED LASER BEAM

This application is a continuation-in-part of U.S. patent application Ser. No. 11/968,589, filed Jan. 2, 2008, entitled "System and Method for Scanning a Pulsed Laser Beam," which is incorporated here by reference in its entirety. This application claims priority to the above-referenced application.

FIELD OF THE INVENTION

The field of the present invention generally relates to laser scanners and more particularly, to systems and methods for scanning pulsed laser beams.

BACKGROUND

Pulsed laser beams include bursts or pulses of light, as implied by name, and have been used for photoalteration of materials, both inorganic and organic alike. Pulsed lasers, such as non-ultraviolet, ultra-short pulsed lasers with pulse durations measured in the nanoseconds to femtoseconds range, are often used in ophthalmic surgical procedures. Typically, a pulsed laser beam is focused onto a desired area of the material, such as the cornea, the capsular bag, or the lens of the eye, to photoalter the material in this area and, in some instances, the associated peripheral area. Examples of photoalteration of the material include, but are not necessarily limited to, chemical and physical alterations, chemical and physical breakdown, disintegration, ablation, photodisruption, vaporization, a the like.

One example of photoalteration using pulsed laser beams is the photodisruption (e.g., via laser induced optical breakdown) of a material. Localized photodisruptions can be placed at or below the surface of the material to produce high-precision material processing. For example, a micro-optics scanning system may be used to scan the pulsed laser beams to produce an incision in the material and to create a flap therefrom. The term "scan" or "scanning" refers to the movement of the focal point of a pulsed laser beam along a desired path. To create a flap of the material, the pulsed laser beam is typically scanned along a pre-determined region (e.g., within the material) in either a spiral pattern or a raster pattern. In general, these patterns are mechanically simple to implement (e.g., continuous) and to control for a given scan rate and for a desired focal point separation of the pulsed laser beam. These patterns are also generally efficient.

Despite these advantages, the spiral or raster pattern may impose limits on the creation of a flap (e.g., due to mechanical restrictions on the micro-optic based scanning system or the like). In general, faster scan rates are desirable, but existing laser scanning equipment may lag commanded laser positions along one axis or along both axes, thus, shortening or compressing one or more raster scan lines along another axis. For example, a circular scan area using a raster pattern may become elliptical with faster scan rates. In addition, faster scan rates may result in greater accelerations of the mass associated with the scanning system. These greater accelerations in turn complicate control accuracy. For example, greater accelerations have been observed while scanning the central region of a spiral pattern (e.g., as the spiral tightens). Greater accelerations have also been observed while scanning the periphery of a raster pattern (e.g., as the scanning changes direction with the raster pattern).

As such, systems and methods for scanning a pulsed laser beam that improve scanning control are desirable. More particularly, systems and methods for scanning a pulsed laser beam that reduce accelerations during scanning are desired. There is also a need for systems and methods for creating a flap with a pulsed laser beam operating at increased pulse repetition rates while maintaining or reducing the acceleration associated with scanning the pulsed laser beam.

Moreover, during the well-known LASIK (Laser-Assisted in Situ Keratomileusis) procedure, a pulsed laser is used to create a flap in the cornea to expose the corneal stroma, which is then photoablated with an excimer laser to correct vision problems such as myopia, hyperopia, astigmatism, and the like. Scanning an ultra-short wavelength pulsed laser beam over the cornea of a patient's eye creates contiguous small bubbles that expand to form a resection plane for the flap. The small gas bubbles are released when the corneal flap is lifted, so they do not interfere with the excimer laser's photoablation process. But, sometimes the gas bubbles diffuse through and accumulate, forming an opaque bubble layer ("OBL") in the corneal flap bed. The OBL does not release when the flap is lifted, and a result, may interfere with flap creation and/or with the excimer laser's iris recognition capabilities, which are generally used for proper alignment and positioning of the laser beam. Since the OBL typically remains in the corneal flap bed for up to ten or more minutes, iris recognition errors may be as high as 10%, which may consequently affect the precision, accuracy, and effectiveness of the laser procedure and the surgical outcome. Therefore, it is also desirable to provide systems and methods for reducing and/or eliminating the formation of opaque bubble layers in the corneal flap bed.

SUMMARY OF THE INVENTION

Embodiments of the present invention are directed towards photoaltering a material using a pulsed laser beam. In one embodiment, a method of photoaltering a region of a material using a pulsed laser beam is provided. The method includes scanning the pulsed laser beam in a first portion of the region with a first pattern, scanning the pulsed laser beam in a second portion of the region with a second pattern, and separating a flap of the material at the region. The first pattern has a first maximum acceleration associated with the region, and the second pattern has a second maximum acceleration less than the first maximum acceleration.

In another embodiment, a system for photoaltering a region of the material is provided. The system includes a laser configured to produce a pulsed laser beam, a controller configured to select at least a first pattern and a second pattern, and a scanner coupled to the controller. The first pattern has a first maximum acceleration associated with the second portion, and the second pattern has a second maximum acceleration associated with the second portion. The second maximum acceleration is less than the first maximum acceleration. The scanner is operable to scan the pulsed laser beam in a first portion of the region with the first pattern, and scan the pulsed laser beam in a second portion of the region with the second pattern.

In yet another embodiment, a system and method for photoaltering a region of the material, such as the cornea, are provided so as to reduce and/or eliminate the opaque bubble layer (OBL) in the corneal flap bed.

This summary and the following detailed description are merely exemplary, illustrative, and explanatory, and are not intended to limit, but to provide further explanation of the invention as claimed. Additional desirable features, advantages, and characteristics of the present invention will be set forth in the detailed descriptions, the claims, and the accompanying drawings that follow, and in part, will be apparent from the descriptions, or may be learned by practicing various embodiments of the invention. All additional systems, methods, features and advantages are intended to be included within the scope of the invention, and to be protected by the accompanying claims and their equivalents.

BRIEF DESCRIPTION OF THE DRAWINGS

In the drawings, wherein like reference numerals refer to similar components:

FIGS. 10(a) through 10(d) show a top view of a seventh compound scan pattern according to another embodiment;

DETAILED DESCRIPTION

Figure 1:
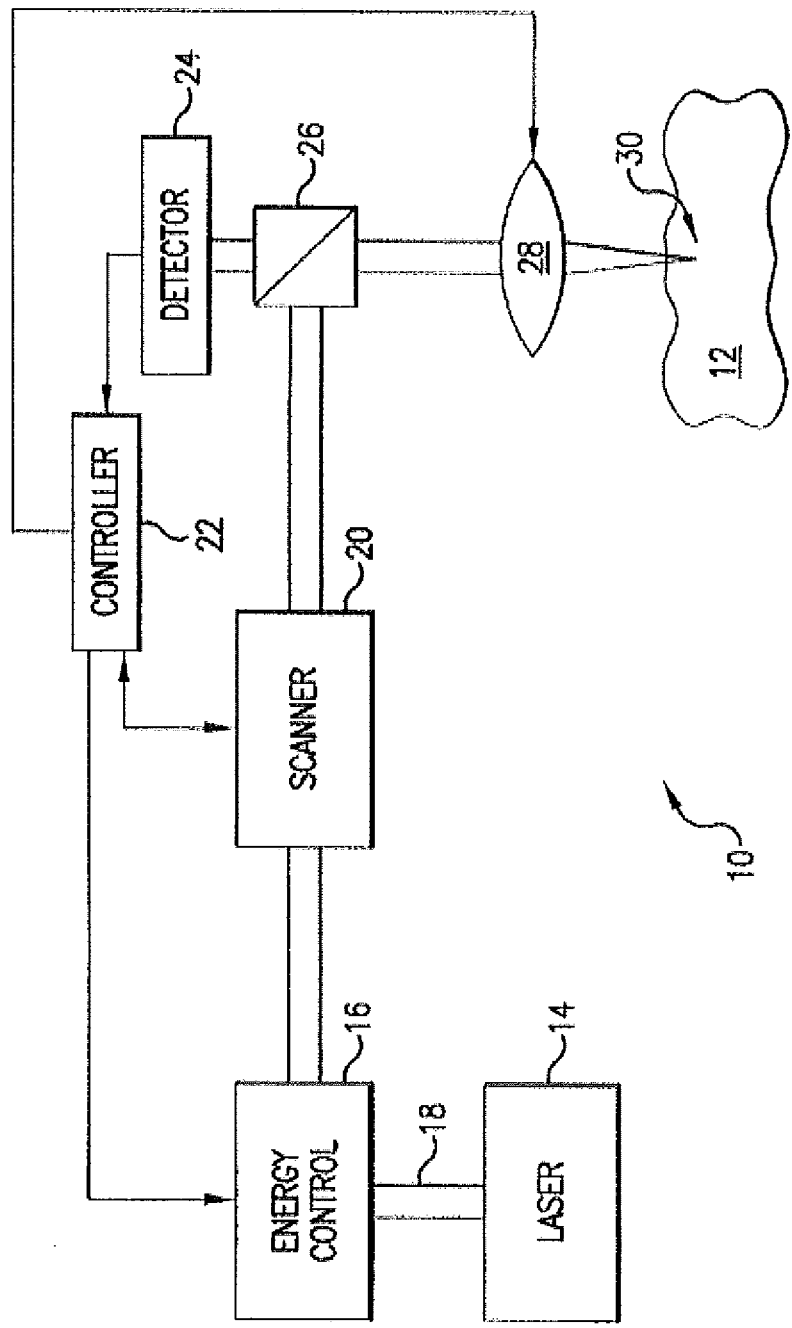
FIG. 1 is a block diagram of a laser scanner system according to one embodiment of the present invention.

This disclosure is directed to all applicable variations, changes, and modifications known to those skilled in the art. As such, the following detailed description is merely illustrative and exemplary in nature, and is neither intended to limit the embodiments of the subject matter, nor the uses of those embodiments. The terms "exemplary" and "illustrative" mean "serving as an example, an instance, or an illustration." Any implementation described as exemplary or illustrative is not meant to be construed as preferred or advantageous over other implementations. Nor is there any intent to be bound by any expressed or implied theory presented in the background, summary, or the detailed description.

Embodiments of the present invention provide systems and methods for scanning a pulsed laser beam that reduce acceleration affects associated therewith, and/or that reduce or eliminate the formation of an opaque bubble layer ("OBL") in a corneal flap bed, which is associated with scanning a pulsed laser beam in certain ophthalmic applications. Photoalteration of a material may be accomplished using a pulsed laser beam that is directed (e.g., via a scanner) at a desired region of the material (e.g., the cornea, the capsular bag, or the lens of a patient's eye in certain ophthalmic applications). For example, a pulsed laser beam may be controlled to scan a desired region in the material to produce a flap. To impart at least a portion of this control, software, firmware, or the like, can be used to command the actions and placement of the scanner via a motion control system, such as a closed-loop proportional integral derivative (PID) control system. In one embodiment, these systems and methods reduce accelerations, as well as the acceleration effects associated with scanning a conventional pattern (e.g., a spiral pattern or a raster pattern), while maintaining a desired scan rate and focal point spatial separation of the pulsed laser beam. The term "acceleration" is defined herein to be the acceleration of a mass associated with a scanning element or a scanning system including, but not necessarily limited to, a laser, a laser scanner, scanning mirrors, a scanning chassis, focusing optics, and any combination thereof. Alternatively, these systems and methods limit the accelerations associated with scanning the conventional pattern while permitting a faster scan rate of the pulsed laser beam.

In another embodiment, blanking is incorporated with the scanning to improve scanning accuracies. The term "blanking" is defined herein to be a prevention of a laser pulse transmission (e.g., via shuttering of the pulsed laser beam). For example, when using a substantially constant laser pulse rate (e.g., for the pulsed laser beam), blanking is used to avoid altering this laser pulse rate and limit overlap of scanned pulse spots. Additionally, blanking may be used to slow the energy deposition rate into the material. In embodiments incorporating blanking, the pulsed laser beam is prevented from scanning over a previous scan (e.g., one or more spots associated with one or more focal points of a pulsed laser beam).

In another embodiment used in ophthalmic applications, these systems and methods may reduce and/or eliminate the formation of an opaque bubble layer in the corneal flap bed of a patient's eye.

Referring to the drawings, FIG. 1 shows a system 10 for photoaltering a material 12. The system 10 includes, but is not necessarily limited to, a laser 14 capable of generating a pulsed laser beam 18, an energy control module 16 for varying the pulse energy of the pulsed laser beam 18, a scanner 20, a controller 22, and focusing optics 28 for directing the pulsed laser beam 18 from the laser 14 on or within the material 12. The controller 22, such as a processor operating suitable control software, is operatively coupled with the scanner 20, the focusing optics 28, and the energy control unit 16 to direct a focal point 30 of the pulsed laser beam along a scan pattern on or in the material 12. In this embodiment, the system 10 further includes a beam splitter 26 and a detector 24 coupled to the controller 22 for a feedback control mechanism of the pulsed laser beam 18. Other feedback methods may also be used, including but not necessarily limited to position encoder on the scanner 20 or the like.

The scanner 20 moves the focal point of the pulsed laser beam 18 in increments through a desired scan pattern as controlled by the controller 22. The step rate at which the focal point is moved is referred to herein as the scan rate. For example, the scanner 20 can operate at scan rates between about 10 kHz and about 400 kHz, or at any other desired scan rate. In one embodiment, the scanner 20 generally moves the focal point of the pulsed laser beam 18 through the desired scan pattern at a substantially constant scan rate while maintaining a substantially constant separation between adjacent focal points of the pulsed laser beam 18. For a given scan pattern or combination of scan patterns (e.g., a compound scan pattern), the time for completing the scan pattern is inversely proportional to the scan rate. Further details of laser scanners are known in the art, such as described, for example, in U.S. Pat. No. 5,549,632, the entire disclosure of which is incorporated herein by reference.

To provide the pulsed laser beam, a chirped pulse laser amplification system, such as that described in U.S. Pat. No. RE37,585, may be used for photoalteration. U.S. Pat. No. 7,351,241 also describes other methods of photoalteration.

Other devices or systems may also be used to generate pulsed laser beams. For example, non-ultraviolet (UV), ultrashort pulsed laser technology can produce pulsed laser beams having pulse durations measured in femtoseconds. Some of the non-UV, ultrashort pulsed laser technology may be used in ophthalmic applications. For example, U.S. Pat. No. 5,993,438 discloses a device for performing ophthalmic surgical procedures to effect high-accuracy corrections of optical aberrations. U.S. Pat. No. 5,993,438 discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point.

Although the system 10 may be used to photoalter a variety of materials (e.g., organic, inorganic, or a combination thereof), the system 10 is suitable for ophthalmic applications in one embodiment. In this case, the focusing optics 28 direct the pulsed laser beam 18 toward an eye (e.g., onto or into a cornea) for plasma mediated (e.g., non-UV) photoablation of superficial tissue, or into the stroma of the cornea for intrastromal photodisruption of tissue. In this embodiment, the system 10 may also include a lens (not shown) to change the shape (e.g., flatten or curve) of the cornea prior to scanning the pulsed laser beam 18 toward the eye. The system 10 is capable of generating the pulsed laser beam 18 with physical characteristics similar to those of the laser beams generated by a laser system disclosed in U.S. Pat. No. 4,764,930, U.S. Pat. No. 5,993,438, or the like.

For example, the ophthalmic laser system 10 can produce an ultra-short pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam 18 has a wavelength that permits the pulsed laser beam 18 to pass through the cornea without absorption by the corneal tissue. The wavelength of the pulsed laser beam 18 is generally in the range of about 3 μm to about 1.9 nm, preferably between about 400 nm to about 3000 nm, and the irradiance of the pulsed laser beam 18 for accomplishing photodisruption of stromal tissues at the focal point is typically greater than the threshold for optical breakdown of the tissue. Although a non-UV, ultrashort pulsed laser beam is described in this embodiment, the pulsed laser beam 18 may have other pulse durations and different wavelengths in other embodiments.

For ophthalmic applications, the scanner 20 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis. In preparing a corneal bed for flap separation, for example, a circular area may be scanned using a scan pattern driven by the scanning mirrors. In another embodiment, a dome-shaped area may be scanned using a three-dimension movement (e.g., along the x-, y-, and z-axes) driven by the scanning mirrors. The pulsed laser beam 18 photoalters the stromal tissue by scanning the focal point of the pulsed laser beam 18 in a pattern of spots (e.g., based on the scan pattern), the distribution of which is determined by the pulse frequency, the scan rate, and the amount of scan line separation. Generally, higher scan rates, enable shorter procedure times by increasing the rate at which corneal tissue can be photoaltered. For example, the scan rates may be selected from a range between about 1 kHz and about 1 GHz with a pulse width in a range between about 300 picoseconds and about 10 femtoseconds, although other scan rates and pulse widths may be used.

The system 10 may additionally acquire detailed information about optical aberrations to be corrected, at least in part, using the system 10. Examples of such detailed information include, but are not necessarily limited to, the extent of the desired correction, and the location in the cornea of the eye where the correction can be made most effectively. The refractive power of the cornea may be used to indicate corrections. Wavefront analysis techniques, made possible by devices such as a Hartmann-Shack type sensor (not shown), can be used to generate maps of corneal refractive power. Diagnostic and measurement systems that use a Shack-Hartmann wavefront sensor to quantify aberrations throughout the entire optical system of a patient's eye include the Abbott Wavescan WaveFront™ System, and the Abbott iDesign™ Advanced WaveScan Studio aberrometer. Exemplary Shack-Hartmann type wavefront diagnostic systems are described in commonly-owned U.S. Pat. No. 7,931,271, U.S. Pat. No. 7,931,374, U.S. Pat. No. 8,126,246, which are incorporated here by reference. Other wavefront analysis techniques and sensors may also be used, such as Tscherning based aberrometry, ray tracing type wavefront analysis (e.g., Tracey VFA), and spatial skiametry (e.g., Nidek OPD-Scan). The maps of corneal refractive power, or similar refractive power information provided by other means, such as corneal topography or the like, can then be used to identify and locate the optical aberrations of a cornea that require correction.

When the laser 14 is activated, the focal spot 30 of the pulsed laser beam 18 is selectively moved (e.g., via the scanner 20) along a beam path to photoalter stromal tissue, also referred to herein as scanning For example, the focal spot 30 of the pulsed laser beam 18 is selectively directed along a predetermined length of the beam path in one reference area. The pulsed laser beam 18 is then redirected through another reference area, and the process of photoalteration is repeated. The sequence for directing the pulsed laser beam 18 through individually selected reference areas can be varied, and the extent of stromal tissue photoalteration while the incising laser beam is so directed, can be varied. Specifically, as indicated above, the amount of photoalteration can be based on the refractive power map. On the other hand, the sequence of reference areas that is followed during a customized procedure will depend on the particular objectives of the procedure.

Scanning may be applied using one or more scan patterns to one or more combinations of these reference areas. One example of an ophthalmic scanning application is a laser in-situ keratectomy (LASIK) type procedure where a flap is cut from the cornea to establish extracorporeal access to the tissue that is to be photoaltered. The flap may be created using one or more scan patterns of pulsed laser beams. To create the corneal flap, a sidecut is created around a desired perimeter of the flap such that the ends of the sidecut terminate, without intersection, to leave an uncut segment. This uncut segment serves as a hinge for the flap. The flap is separated from the underlying stromal tissue by scanning the laser focal point across a resection bed, the perimeter of which is approximately defined by and slightly greater than the sidecut. Once this access has been achieved, photoalteration is completed, and the residual fragments of the photoaltered tissue are removed from the cornea. Additionally, the pulsed laser beams may be scanned to customize the incisions, such as for shaped incisions with advanced edge profiles (e.g., Intralase-enabled keratoplasty (IEK)). In another embodiment, intrastromal tissue may be photoaltered by the system 10 so as to create an isolated lenticle of intrastromal tissue. The lenticle of tissue can then be removed from the cornea to alter the healed curvature of the cornea and change the corresponding refractive properties.

Generally, to create a flap in ophthalmic applications, the pulsed laser beam 18 is scanned at a substantially constant scan rate while maintaining a substantially constant separation between adjacent focal points of the pulsed laser beam 18. In one embodiment, the controller 22 directs the scanner 20 to scan the pulsed laser beam 18 along a compound scan pattern that includes two or more scan patterns for the desired region of photoalteration (e.g., a resection bed). These scan patterns are preferably selected (e.g., by the controller 22) such that high acceleration regions normally associated with a first scan pattern are substituted by a second scan pattern. The second scan pattern is selected such that scanning the second scan pattern in the high acceleration region (i.e., associated with the first scan pattern) is accomplished with a lower acceleration (e.g., less than a maximum acceleration associated scanning the high acceleration region), while maintaining a substantially constant scan rate of the pulsed laser beam 18. Although, the compound scan pattern is described with two different scan patterns, multiple scan patterns may be used.

Additionally, the system 10 may use blanking with portions of one or more of scan patterns to reduce repetitious scans of the same spot. While scanning a pulsed laser beam normally produces a substantially continuous train of laser pulses, blanking may be incorporated to selectively prevent one or more of the pulses of the pulsed laser beam from being scanned over a prior scan spot. For example, while scanning a train of pulses, the relative position of the scanner 20 (e.g., relative scanning mirror(s) position) associated with each scan spot may be recorded for a particular procedure, timely compared with subsequent laser pulses. Subsequent laser pulses that might overlap with prior scan spots may then be blanked. In one embodiment, the relative position of the scanner 20 may be predicted for each scan spot based on a substantially constant laser pulse rate for a selected scan pattern and thus, blanking can be pre-determined for subsequent laser pulses.

Figure 2:
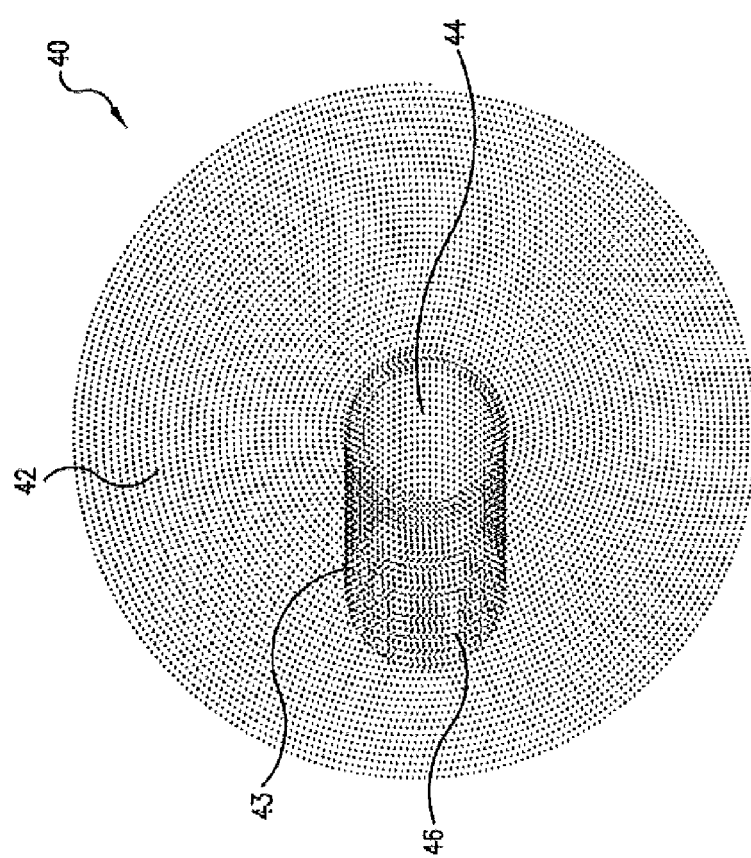
FIG. 2 is a top view of a first compound scan pattern according to one embodiment.
Figure 3:
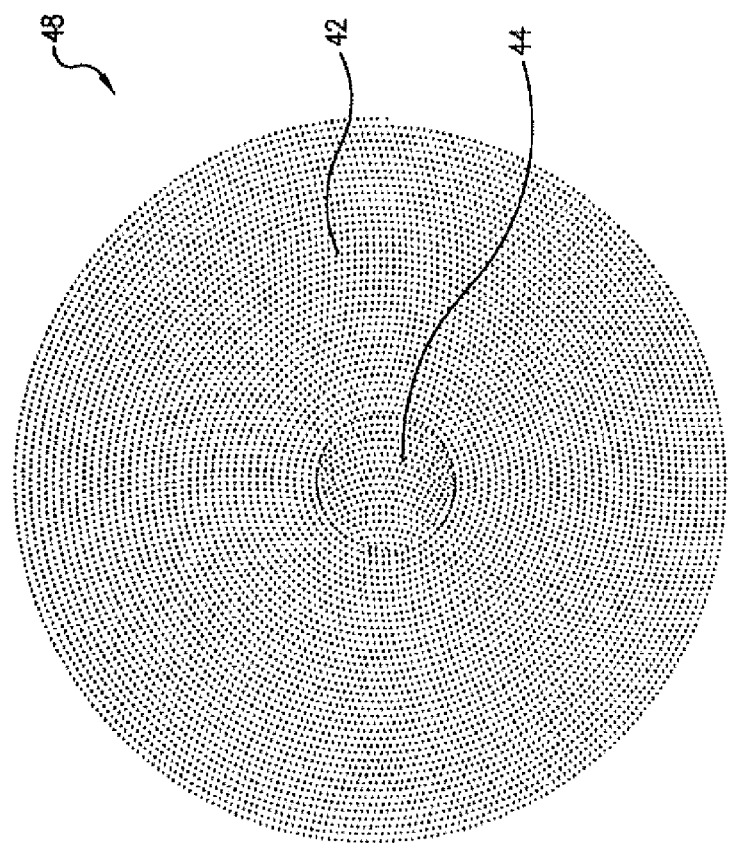
FIG. 3 is a top view of a second compound scan pattern according to another embodiment.

Some examples of compound scan patterns include a spiral scan pattern having a central area with a traveling circular scan pattern, a sinusoidal scan pattern, a progressive oval scan pattern, a spiral scan pattern having a raster scan pattern, or the like. FIG. 2 is a top view of a first compound scan pattern 40 according to one embodiment. The first compound scan pattern 40 includes a spiral scan pattern 42 and a traveling circular scan pattern 43. The traveling circular scan pattern 43 can be produced by scanning multiple circles while traversing in a linear direction after substantially completing each full circle. A first portion 46 of the traveling circular scan pattern 43 overlaps the spiral scan pattern 42, and a second portion 44 of the traveling circular scan pattern 43 occupies a central region of the first compound scan pattern 40 (e.g., a substantially circular central area). FIG. 3 is a top view of a second compound scan pattern 48 according to another embodiment. The second compound scan pattern 48 includes the spiral scan pattern 42 and the second portion 44 of the traveling circular scan pattern 43 occupying a central region (e.g., a substantially circular central area) of the second compound scan pattern 48, both shown in FIG. 2, but omits (e.g., via blanking) the first portion 46 of the traveling circular scan pattern 43. The traveling circular scan pattern 43 has a substantially constant acceleration associated with the circular shape.

Figure 4:
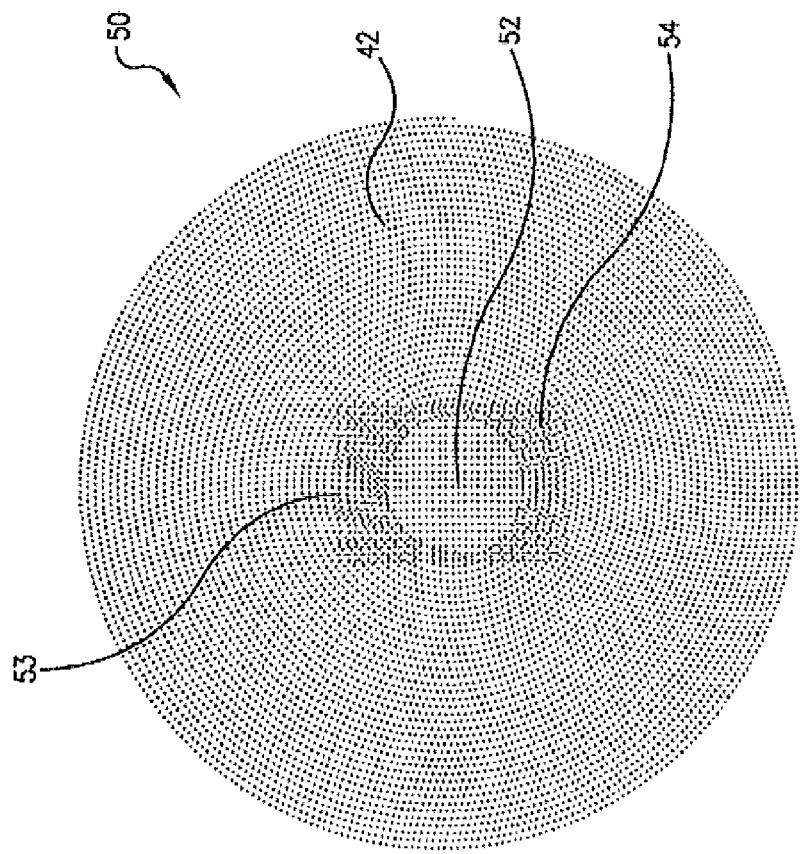
FIG. 4 is a top view of a third compound scan pattern according to another embodiment.
Figure 5:
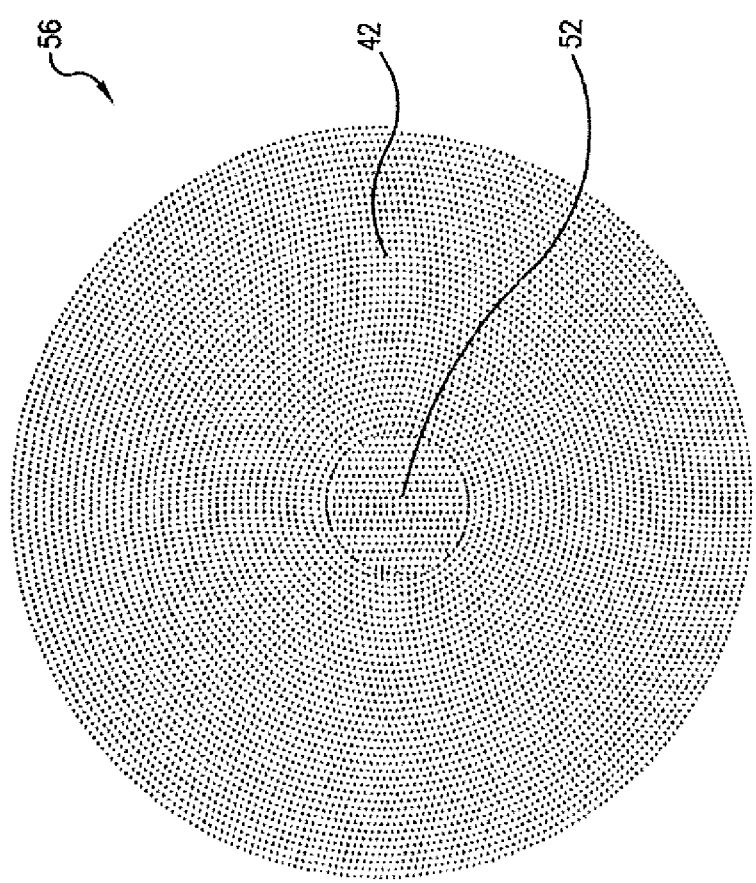
FIG. 5 is a top view of a fourth compound scan pattern according to another embodiment.

FIG. 4 is a top view of a third compound scan pattern 50 according to another embodiment. The third compound scan pattern 50 includes the spiral scan pattern 42 shown in FIG. 2 and a sinusoidal scan pattern 53. For simplicity of illustration, the sinusoidal scan pattern 53 travels linearly along the horizontal axis and is shown in a compressed configuration (e.g., compressed along the horizontal axis) having a relatively high frequency appearance but may be elongated or further compressed for a selected spot separation. A first portion 54 of the sinusoidal scan pattern 53 overlaps the spiral scan pattern 42, and a second portion 52 of the sinusoidal scan pattern 53 occupies a central region (e.g., a substantially circular central area) of the third compound scan pattern 50 (e.g., a substantially circular central area). The sinusoidal scan pattern 53 is scanned such that the deflections of the sinusoidal scan pattern 53 (e.g., the crests of a sine wave) are scanned outside of the central region. In this embodiment, the second portion 52 of the sinusoidal scan pattern 53 (occupying the central region) has a substantially constant acceleration associated with the substantially linear segments of the sine wave. FIG. 5 is a top view of a fourth compound scan pattern 56 according to another embodiment. The fourth compound scan pattern 56 includes the spiral scan pattern 42 and the second portion 52 of the sinusoidal scan pattern 53 occupying a central region (e.g., a substantially circular central area) of the fourth compound scan pattern 56, both shown in FIG. 4, but omits (e.g., via blanking) the first portion 54 of the sinusoidal scan pattern 53.

Figure 6:
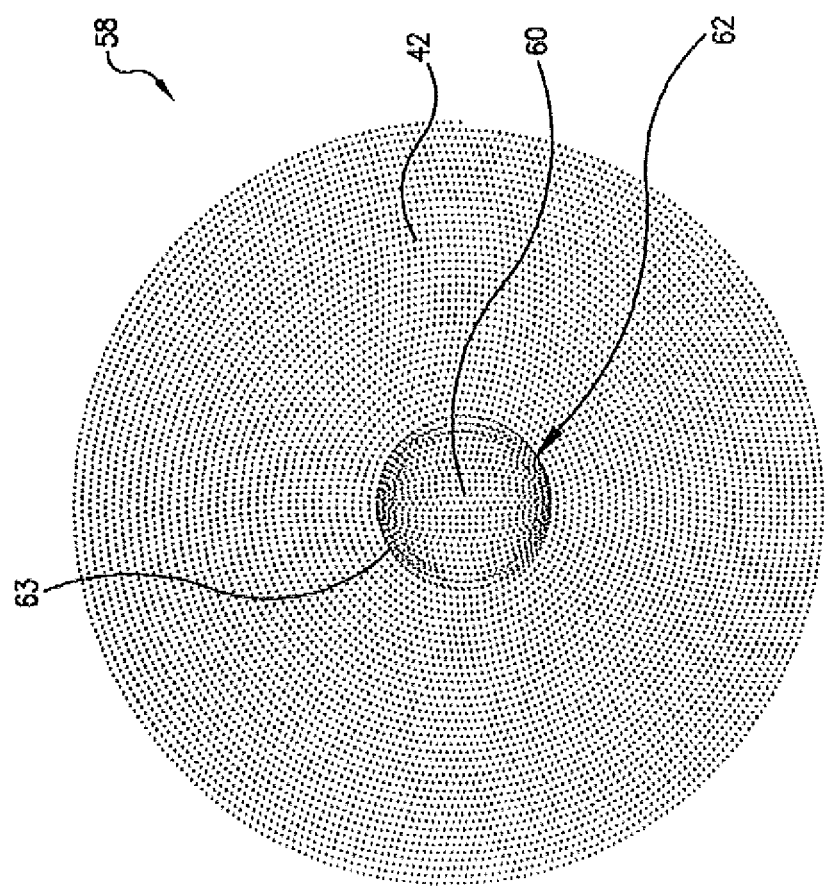
FIG. 6 is a top view of a fifth compound scan pattern according to another embodiment.
Figure 7:
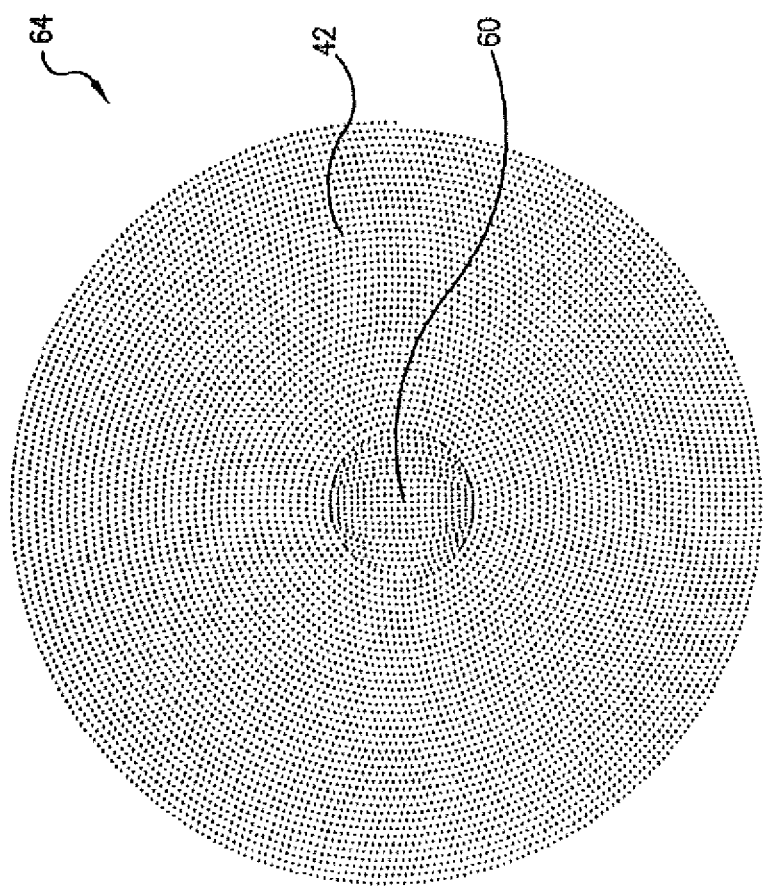
FIG. 7 is a top view of a sixth compound scan pattern according to another embodiment.

FIG. 6 is a top view of a fifth compound scan pattern 58 according to another embodiment. The fifth compound scan pattern 58 includes the spiral scan pattern 42 shown in FIG. 2 and a progressive oval scan pattern 63 occupying a central region of the fifth compound scan pattern 58. The progressive oval scan pattern 63 has a self-overlapping portion 62 and a non-overlapping portion 60. The progressive oval scan pattern 63 is scanned such that an oval shape (having substantially fixed and spaced apart opposing curved apexes) scan progressively contracts or progressively expands with each completed pass of the oval shape. The curved apexes of the oval shape are associated with lower accelerations. FIG. 7 is a top view of a sixth compound scan pattern 64 according to another embodiment. The sixth compound scan pattern 64 includes the spiral scan pattern 42 and the non-overlapping portion 60 of the progressive oval scan pattern 63, both shown in FIG. 6, but omits the self-overlapping portion 62 (e.g., via blanking)

Figure 8:
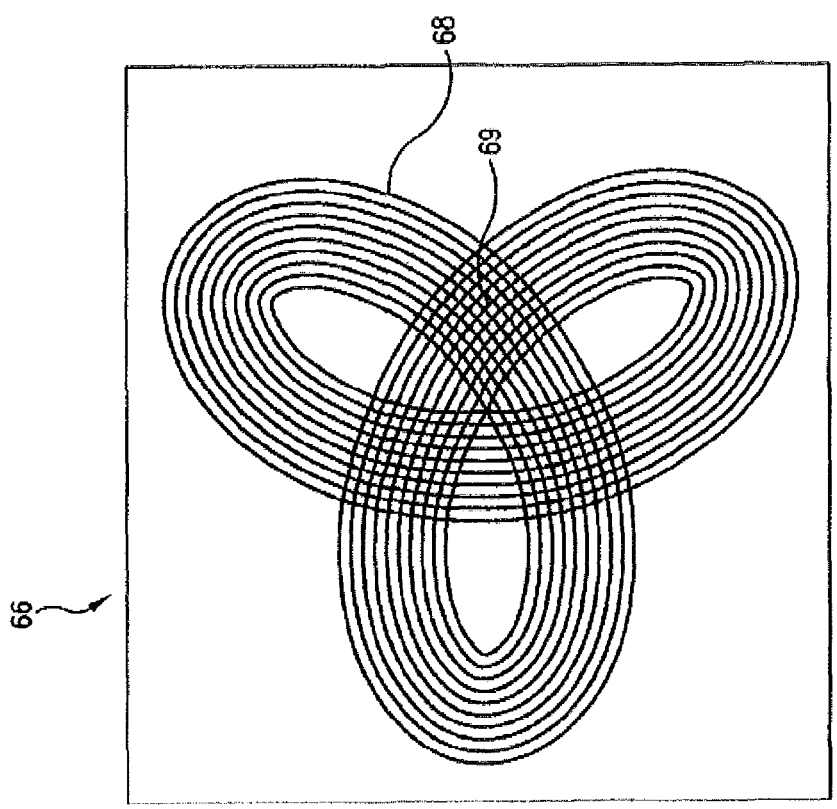
FIG. 8 is a top view of a hypotrochoid scan pattern according to another embodiment.

FIG. 8 is a top view of a hypotrochoid scan pattern 66 according to another embodiment. Referring to FIGS. 2-8, the hypotrochoid pattern 66 can be incorporated with a spiral scan pattern, such as the spiral scan pattern 42, to produce another compound scan pattern. In one embodiment, the hypotrochoid scan pattern is scanned such that a hypotrochoid shape progressively contracts or progressively expands with each pass of the hypotrochoid shape. The hypotrochoid scan pattern 66 has a central region 68 that may be used when scanning the high acceleration region of the spiral scan pattern (e.g., such as associated with the central regions 44, 52, and 60). For example, the hypotrochoid scan pattern 66 may be scanned over a high acceleration region such that the central region 68 overlays the high acceleration region. Blanking may also be used to omit scanning portions of the hypotrochoid scan pattern 66 over the spiral scan pattern.

Additionally, blanking can be used to avoid double scanning rhomboid shaped self-overlapping regions 69 within the hypotrochoid pattern 66. The curved apexes of the hypotrochoid shape are associated with lower accelerations.

Figure 9B:
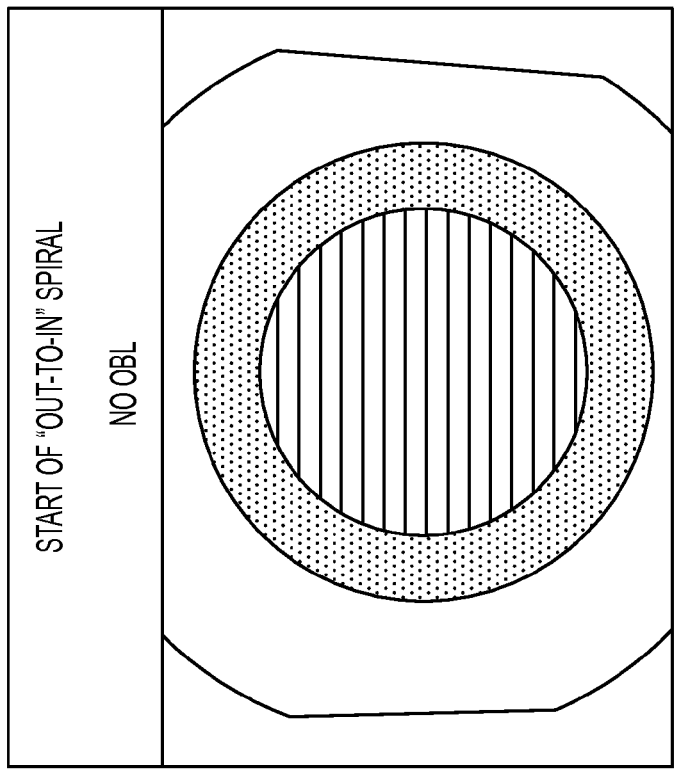
FIGS. 9(a) and 9(b) show two exemplary results of scanning in some ophthalmic surgeries.
Figure 9A:
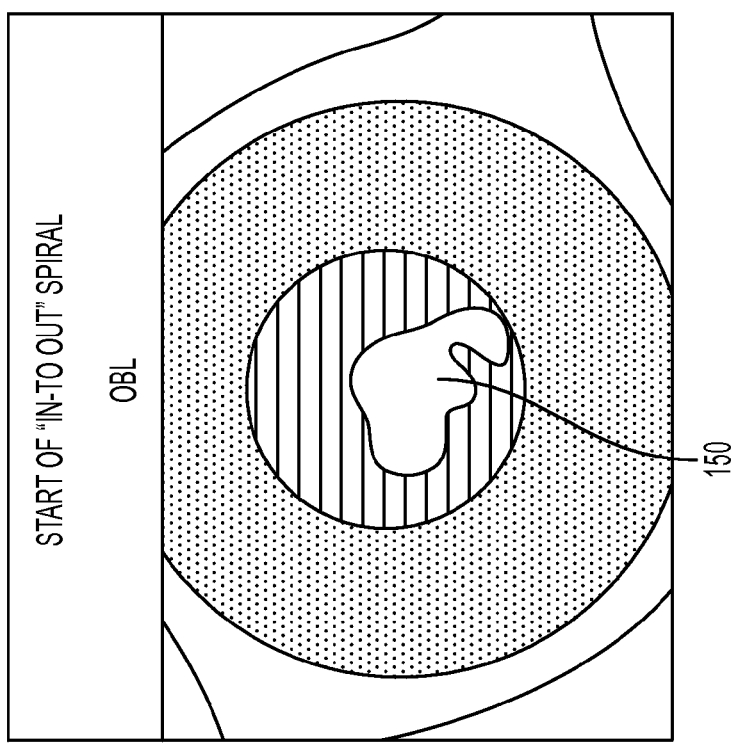

During ophthalmic surgery, the compound scan patterns in FIGS. 2-8 may form an accumulation of gas bubbles or an OBL 150 in the bed of the corneal flap, as shown in FIG. 9(a), especially when the first or second pattern is a spiral pattern or a traveling circular scan pattern with the scan starting from the center and progressing outward. When the scan starts from the outer edge (e.g., the periphery of the region) and progresses inward (e.g., toward the center of the region), however, there is often no OBL, as shown in FIG. 9(b). In the periphery-to-inward spiral pattern scanning of FIG. 9(b), the round trip time of the circle at the outer edge, e.g., 8-9 mm in circumference, is much longer than that of the circle near the center. Therefore, the ablation gas has sufficient time to either cool down or to migrate away before the next circle of the spiral pattern. As such, no OBL is formed.

Figure 11:
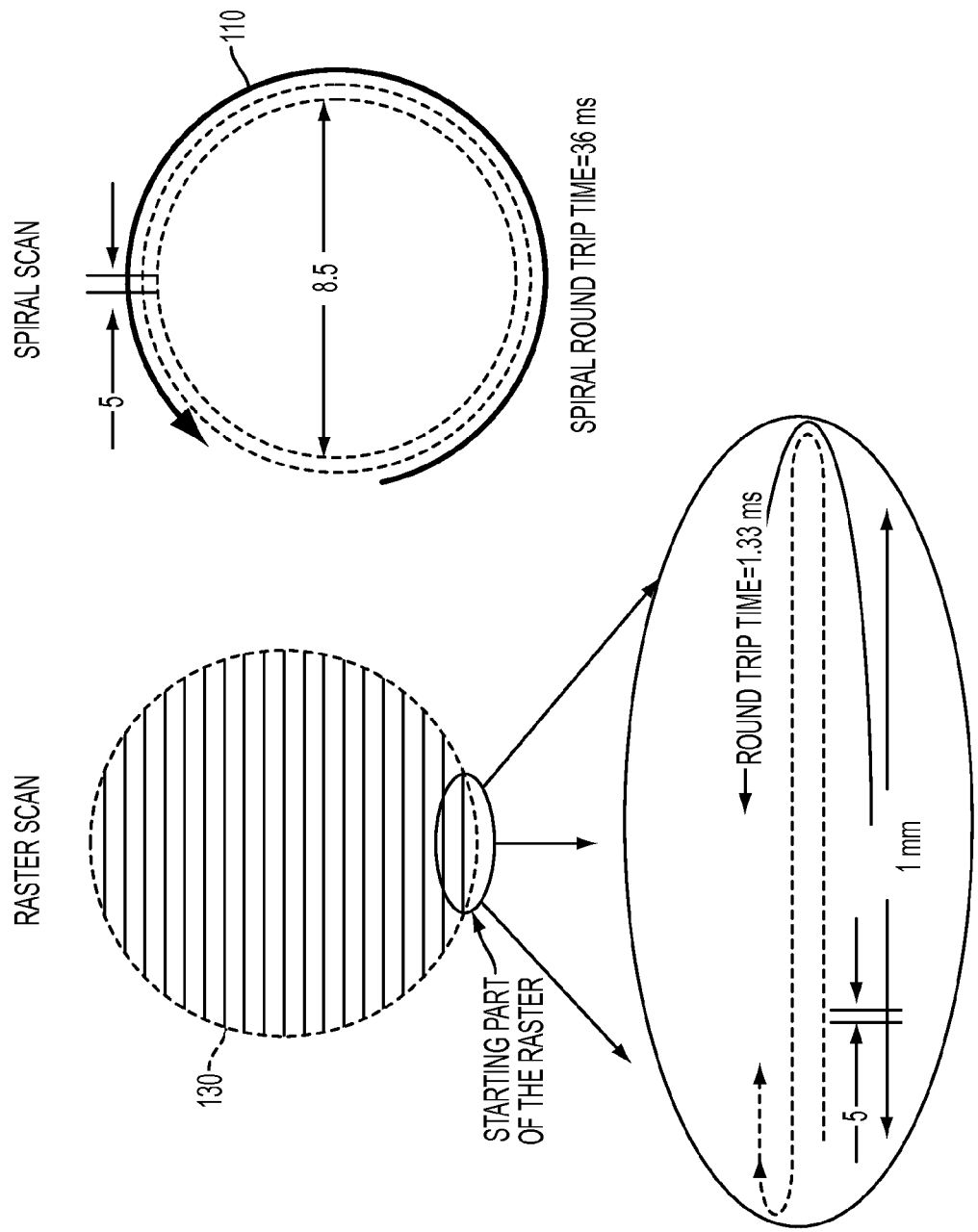
FIG. 11 is an exemplary top view of the seventh compound scan pattern according to another embodiment.

FIGS. 10(a) through 10(d) illustrate a top view of a seventh compound scan pattern 100 according to another embodiment. The compound scan pattern 100 includes the spiral scan pattern 110 of FIG. 10(a) and a raster scan pattern 130 of FIG. 10(b) occupying a central region 120 of the compound scan pattern 100. A first portion 131 of the raster scan pattern 130 overlaps with the spiral scan pattern 110, and a second portion 132 of the raster scan pattern 130 occupies the central region 120 of the compound scan pattern 100 (e.g., a substantially circular central area), as shown in FIG. 10(d). In this embodiment, the second portion 132 of the raster scan pattern 130 (occupying the central region) has a substantially constant acceleration. The spiral scan pattern 110 serves as a "pocket" for the raster scan, buffering the gas upon the start of the scanning of the raster scan pattern 110. A side cut 140, performed after the spiral scan pattern 110 and the raster scan pattern 130, forms the corneal flap. FIG. 10(d) shows the top view of the superposition of the spiral scan pattern 110, the raster scan pattern 130, and the side cut 140. In an exemplary embodiment, the spiral scan pattern 110 has an outer diameter of about 8.5 mm, and an inner diameter of about 7 mm. The raster scan pattern 130 has a diameter of about 7.1 mm. As such, there is about a 50 μm to 100 μm horizontal overlap 131 between the spiral scan pattern 110 and the raster scan pattern 130. The side cut 140 has a diameter of about 8.4 mm. In this exemplary embodiment, as FIG. 11 shows, with an exemplary 150 kHz laser, the roundtrip time of the spiral scan at the start of the spiral scan pattern 110 is about 36 ms. The roundtrip time of the approximately 1 mm horizontal length at the start of the raster scan pattern 130 (e.g. at the bottom of the raster scan pattern 130) is only about 1.33 ms. Hence, the time difference, e.g., between 36 ms and 1.33 ms, is long enough to prevent the formation of the OBL.

Alternatively, the compound scan pattern 100, having the spiral scan pattern 110 and a raster scan pattern 130, may also be combined with the use of deep stromal pockets below the hinge of the flap. For the raster scan pattern 130, the raster scanning may also be sinusoidal as the scanning travels along the horizontal axis.

Figure 12:
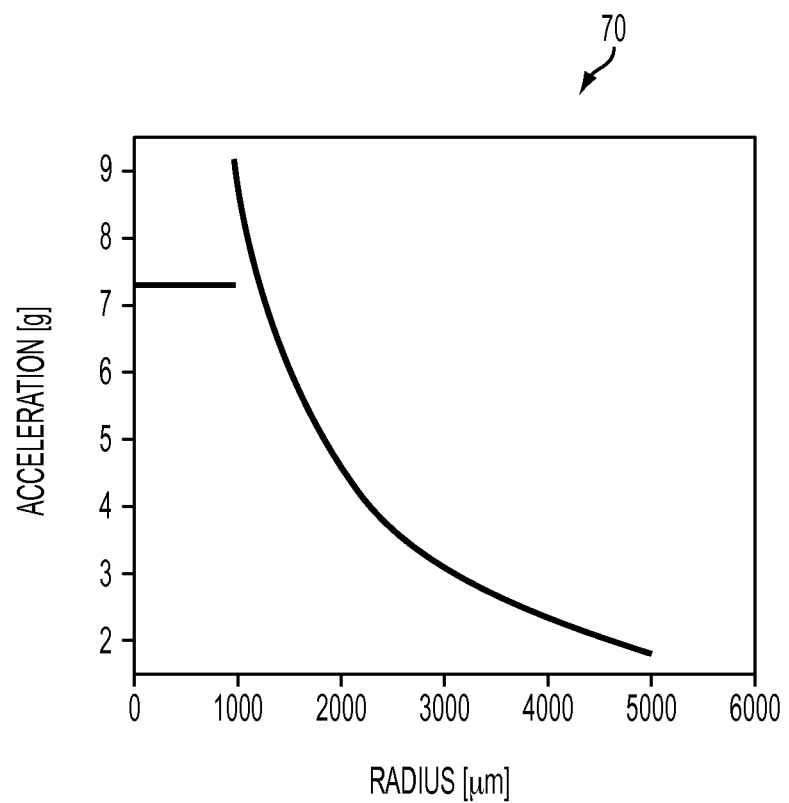
FIG. 12 is a graph of acceleration versus distance for a compound scan pattern according to one embodiment.

FIG. 12 is a plot 70 of acceleration versus distance for a compound scan pattern illustrating a reduction in acceleration for a central region of the compound scan pattern according to one embodiment. The compound scan pattern includes a first scan pattern and a second scan pattern. Referring to FIGS. 2-12, the compound scan pattern of this embodiment can be any one of the compound scan patterns 40, 48, 50, 56, 58, 64, and 100 or other compound scan patterns based on a combination of a spiral scan pattern and a second scan pattern (e.g., the hypotrochoid scan pattern 68 or the like). For example, the spiral scan pattern 42 or 110 is located in the periphery of the compound scan pattern, and the second scan pattern is located in the central region of the compound scan pattern, such as the central regions 44, 52, 60, and 120. In this embodiment, the central region radially extends outward from the center of the spiral scan pattern 42 to about 1000 μm.

The compound scan pattern is preferably scanned at a substantially constant scan rate to simplify control, for example. As scanning (i.e., the spiral scan pattern) approaches the central region, the acceleration generally increases. For example, as the spiral scanning becomes narrower, the acceleration movement of the scanning element or scanning system significantly increases. Scanning of the second scan pattern preferably initiates when the acceleration associated with scanning the first scan pattern reaches a predetermined maximum limit. This limit may be selected based on one or more factors, such as mechanical limitations of the system 10, an overall procedure time to complete the scanning (e.g., of the entire scan region), the scan rate, historical data corresponding to a departure from a desired scanning quality, flap quality, uniformity of scan spot separation or scan line separation, or the like.

In this embodiment, the second scan pattern begins at about 1000 μm from the center of the scan region and has a substantially constant acceleration associated therewith. For example, each of the traveling circular scan pattern 43, the sinusoidal scan pattern 53, and the progressive oval scan pattern 63 has a maximum acceleration associated with scanning the respective pattern in the central regions 44, 52, and 60, respectively, and these maximum accelerations are each less than the maximum acceleration associated with scanning the spiral scan pattern 42 in the same region. As best shown in FIG. 12, the second scan pattern has a maximum acceleration (e.g., about 7.3 g), associated with the scanning thereof in a central region of a compound scan pattern, that is substantially less than the maximum acceleration of the spiral pattern (e.g., about 9.4 g) associated with scanning the spiral scan pattern beyond the central region, or in the periphery, of the compound scan pattern (e.g., at about 1000 μm). The maximum acceleration of the second scan pattern would also be substantially less than any extrapolated maximum acceleration (not shown) associated with scanning of the spiral scan pattern in the central region. The compound scan pattern thus reduces acceleration effects normally associated with solely scanning a conventional spiral scan pattern.

In effect, the first scan pattern (e.g., the spiral scan pattern 42) is scanned in a first sub-region (e.g., the periphery of a desired scan region), and the second scan pattern (e.g., the traveling circular scan pattern 44, the sinusoidal scan pattern 52, the progressive oval scan pattern 60, or the like) is scanned in a second sub-region (e.g., a central area) of the desired scan region. For example, the traveling circular scan pattern 44, sinusoidal scan pattern 52, or progressive oval scan pattern is scanned in a substantially circular central region 44, 52, or 60, respectively, that corresponds to the high acceleration region of the spiral pattern. While the compound scan patterns 40, 48, 50, 56, 58, and 64 are illustrated as being scanned within a substantially circular scan region, the scan region may take a variety of shapes and thus, other compound scan patterns may be used to scan different shaped scan regions.

For most of the compound scan patterns, the second scan pattern progresses from a starting point at one location of the second sub-region to a completion point at a different location of the second sub-region. An amount of time (e.g., a time lag) is expended to scan the second sub-region with the second scan pattern. During this time, the material (e.g., the cornea)

may move, expand, stretch, or relax due to the biomechanical change induced in the material by the pulsed laser beam 18. The greater the time expended to cease the progression of an incision and finish the incision with the subsequent compound segment, the greater the effect associated with this movement. For example, corneal tissue movement can manifest as a ridge at the boundary of compound segments, which may adversely affect the optical imaging properties of the treated corneal tissue. Uninterrupted compound patterns may be selectively applied to alleviate this time lag.

With uninterrupted compound patterns, the scanning progression is substantially continuous from completing of the first sub-region scan to initiating the second sub-region scan. In one embodiment, the scanning progression within one sub-region does not cease at any time or at any part of the sub-region boundary. The maximum amount of time lag is on the order of one turn-around of the pulsed laser beam (e.g., a few milliseconds), instead of a much longer time lag associated with interrupted compound patterns. The hypotrochoid scan pattern 66 and the progressive oval scan pattern 63 are examples of uninterrupted patterns, and the traveling circular scan pattern 43 is an example of an interrupted pattern.

By minimizing or eliminating higher accelerations of the scanning system, scanning accuracy of the pulsed laser beam is increased. Additionally, vibrations that may be associated with such higher accelerations can be reduced to improve reliability of the scanning system. By minimizing or eliminating higher accelerations, the pulsed laser beam may operate with higher laser repetition rates and thus, reduce procedure times (e.g., associated with creating a desired scan region).

In general, the temporal sequence of various sub-patterns is not related to the overall limit on the maximum acceleration or procedure time. The temporal sequence is preferably determined by other considerations. One example of such considerations is to provide an exhaust for gas that may be formed during plasma created laser incisions (e.g., U.S. Pat. No. 6,676,653) for the sub-pattern that is first created in the temporal sequence.

Figure 13:
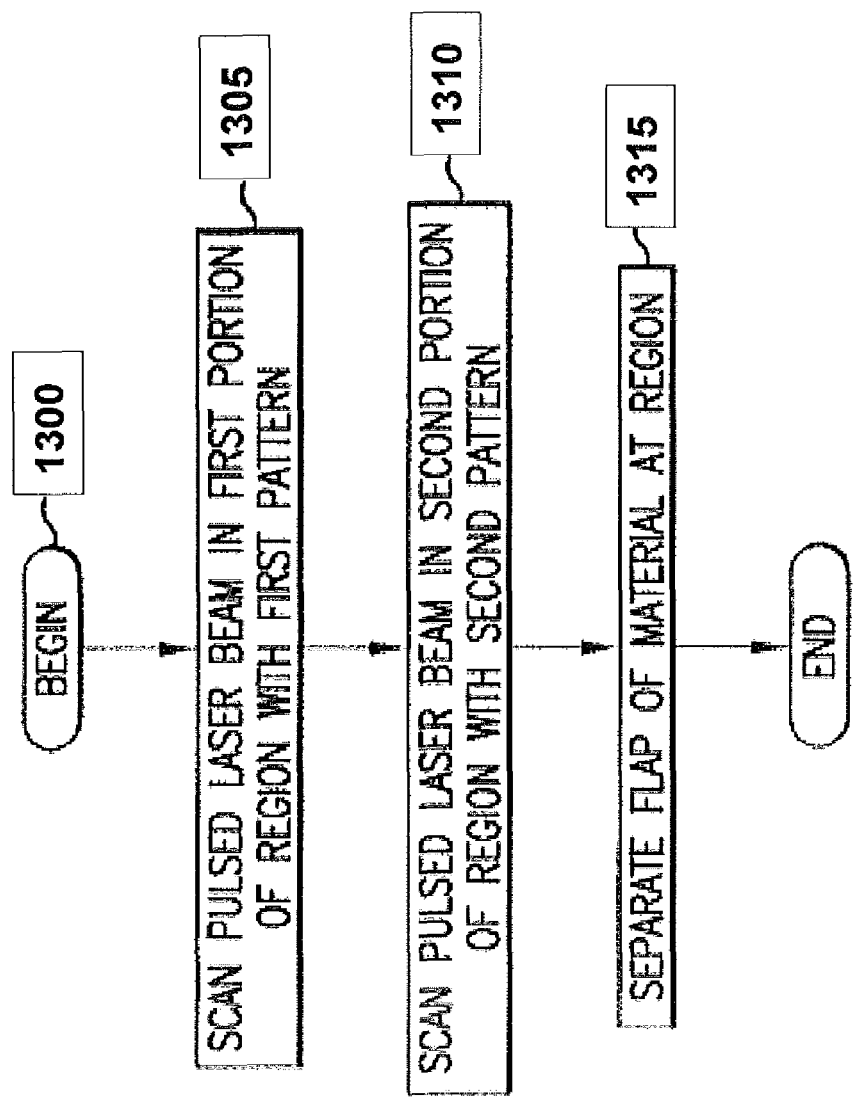
FIG. 13 is a flow diagram of a method for photoaltering a material according to one embodiment.

FIG. 13 is a flow diagram of a method 1300 for photoaltering a region of a material using a pulsed laser beam according to one embodiment. The pulsed laser beam is scanned in a first portion of the region with a first pattern, as indicated at 1305. The pulsed laser beam is scanned in a second portion of the region with a second pattern, as indicated at 1310. A flap of the material (e.g. the cornea of a patient's eye) is separated at the region, as indicated at step 1315.

In one embodiment, the first pattern has a maximum scan acceleration associated with scanning the first pattern in the region, the second pattern has a maximum scan acceleration associated with scanning the second pattern in the second portion, and the maximum scan acceleration of the second pattern is less than the maximum scan acceleration of the first pattern. In another embodiment, the first pattern has a maximum scan acceleration associated with scanning the first pattern in the second portion, the maximum scan acceleration of the second pattern is associated with scanning the second pattern in the second portion, and the maximum scan acceleration of the second pattern is less than the maximum scan acceleration of the first pattern.

At least some of the second portion of the region may overlap with at least some of the first portion of the region to form a third portion of the region. In this embodiment, the pulsed laser beam is blanked while scanning the pulsed laser beam with the second pattern in the third portion. The region may also have a periphery. In this embodiment, the pulsed laser beam is scanned in the first portion in a spiral pattern beginning from the periphery of the region.

The pulsed laser beam may be scanned in an uninterrupted compound pattern. Referring to FIGS. 2-13, the pulsed laser beam may be scanned in the second portion in the traveling circular scan pattern 43, the sinusoidal scan pattern 53, the progressive oval scan pattern 63, or the raster scan pattern 130, for example. Additionally, the pulsed laser beam may be blanked when the traveling circular pattern 43 overlaps the spiral scan pattern 42, when the sinusoidal scan pattern 53 overlaps the spiral scan pattern 42, when the progressive oval scan pattern 63 overlaps itself, or when the raster scan pattern 130 overlaps the spiral scan 110.

Referring to FIGS. 1 and 13, the system 10 may be used to photoalter the material using a pulsed laser beam 18. For example, the pulsed laser beam 18 may be scanned (with either the first or second pattern) at a rate between about 1 kHz and about 1 GHz, with a pulsed energy of about 800 nJ/pulse, with a pulse width of between about 300 picoseconds and about 10 femtoseconds, and/or at a wavelength between about 400 nm to about 3000 nm. Additionally, the pulsed laser beam 18 may be scanned at a sub-surface depth of the material 12.

Thus, systems and methods of photoaltering a material with a pulsed laser beam are disclosed that reduce accelerations associated with scanning the pulsed laser beam.

This disclosure is provided in an exemplary form with a certain degree of particularity to enable a person skilled in the art to make and/or use embodiments of the invention. The specific ordering and combination of the processes and structures described are merely illustrative. Those skilled in the art will understand, however, that many modifications, alternative constructions, changes, and variations can be made in the system, method, and parts and steps thereof, without departing from the spirit or scope of the invention. Hence, the disclosure is not intended to be limited to the specific examples and designs that are described. Rather, it should be accorded the broadest scope consistent with the spirit, principles, and novel features disclosed as generally expressed by the following claims and their equivalents.

What is claimed is:

1. A method of photoaltering a sub-surface region of a patient's cornea using a pulsed laser beam to create a corneal flap, the sub-surface region having an outer periphery, a first portion defined within and circumscribed by the periphery, and a second portion smaller than and located within the first portion, the method comprising the steps of:

transmitting the pulsed laser beam with a scanner having a mass in the first portion of the sub-surface region with a first scan pattern defined over a dome-shaped area in the cornea, the first scan pattern requiring a first maximum scanner mass acceleration when traversing the region, wherein the first scan pattern comprises scanning the pulsed laser beam in a spiral pattern beginning from the periphery of the region and successively tracing smaller rotations toward the second portion to permit sufficient time for ablation gas to either cool down or to migrate away before the next inward rotation of the spiral pattern so as to reduce and/or eliminate formation of an opaque bubble layer (OBL) in a corneal flap bed;

transmitting the pulsed laser beam with the scanner in the second portion of the sub-surface region with a second scan pattern defined over the dome-shaped area in the cornea, the second scan pattern requiring a second maximum scanner mass acceleration less than the first maximum scan acceleration, wherein the second scan pattern comprises scanning the pulsed laser beam in a raster pattern; and separating a corneal flap at the region.

2. The method of claim 1, wherein the step of scanning the pulsed laser beam in the first portion comprises scanning the pulsed laser beam with the first scan pattern having the first maximum scan acceleration, the first maximum scan acceleration associated with the second portion, and wherein the step of scanning the pulsed laser beam in the second portion comprises scanning the pulsed laser beam with the second scan pattern having the second maximum scan acceleration, the second maximum scan acceleration associated with the second portion.

3. The method of claim 1, wherein at least some of the second portion of the region overlaps at least some of the first portion of the region to form a third portion of the region, and wherein the step of scanning the pulsed laser beam in the second portion comprises blanking the pulsed laser beam while scanning the pulsed laser beam with the second scan pattern in the third portion.

4. The method of claim 1, wherein the step of scanning the pulsed laser beam in the first portion comprises scanning the pulsed laser beam at a rate between about 1 kHz and about 1 GHz, and wherein the step of scanning the pulsed laser beam in the second portion comprises scanning the pulsed laser beam at a rate between about 30 MHz and about 1 GHz.

5. The method of claim 1, wherein the step of scanning the pulsed laser beam in the first portion comprises scanning the pulsed laser beam with a pulse energy of about 800 nJ/pulse, and wherein the step of scanning the pulsed laser beam in the second portion comprises scanning the pulsed laser beam with a pulse energy of about 800 nJ/pulse.

6. The method of claim 1, wherein the step of scanning the pulsed laser beam in the first portion comprises scanning the pulsed laser beam with a pulse width of between about 300 picoseconds and about 10 femtoseconds, and wherein the step of scanning the pulsed laser beam in the second portion comprises scanning the pulsed laser beam with a pulse width between about 300 picoseconds and about 10 femtoseconds.

7. The method of claim 1, wherein the step of scanning the pulsed laser beam in the first portion comprises scanning the pulsed laser beam at a wavelength between about 400 nm to about 3000 nm, and wherein the step of scanning the pulsed laser beam in the second portion comprises scanning the pulsed laser beam at a wavelength between about 400 nm to about 3000 nm.

8. The method of claim 1, wherein the step of scanning the pulsed laser beam in the second portion comprises scanning the pulsed laser beam in an uninterrupted compound pattern.

9. The method of claim 8, wherein the step of scanning the pulsed laser beam in an uninterrupted compound pattern comprises scanning the pulsed laser beam in a hypotrochoid pattern.

10. The method of claim 1, wherein the step of scanning the pulsed laser beam in the second portion comprises combining scanning the pulsed laser beam with a sinusoidal pattern.

11. The method of claim 10, wherein the step of scanning the pulsed laser beam with a sinusoidal pattern comprises blanking the pulsed laser beam when scanning the sinusoidal pattern where it overlaps the spiral pattern.

12. The method of claim 1, further including transmitting the pulsed laser beam to create a side cut around a desired perimeter of the flap while leaving an uncut segment to serve as a hinge for the flap, and wherein transmission of the pulsed laser beam in the first and second scan patterns forms a resection bed the perimeter of which is approximately defined by and slightly greater than the side cut.

13. A system for photoaltering a sub-surface region of a patient's cornea to create a corneal flap, the sub-surface region having an outer periphery, a first portion defined within and circumscribed by the periphery, and a second portion smaller than and located within the first portion and a periphery, the system comprising:

a laser configured to produce a pulsed laser beam;

a scanner having a mass configured to move and direct the pulsed laser beam into the sub-surface region of the cornea, and the system being configured to produce relative three-dimensional movement of a focal point of the pulsed laser beam relative to a patient's eye and corresponding accelerations of the scanner mass;

a controller configured to control movement of the scanner and direct the pulsed laser beam relative to the patient's eye in at least a first scan pattern defined over a dome-shaped area within the cornea and a second scan pattern defined over a dome-shaped area within the cornea, the first scan pattern requiring a first maximum scanner mass acceleration when traversing the second portion, the second scan pattern requiring a second maximum scanner mass acceleration when traversing the second portion, the second maximum acceleration being less than the first maximum acceleration; and wherein the scanner is operable in response to the controller to:

transmit the pulsed laser beam in the first portion of the sub-surface region with the first scan pattern, wherein the first scan pattern comprises scanning the pulsed laser beam in a spiral pattern beginning from the periphery of the sub-surface region and successively tracing smaller rotations toward the second portion to permit sufficient time for ablation gas to either cool down or to migrate away before the next inward rotation of the spiral pattern so as to reduce and/or eliminate formation of an opaque bubble layer (OBL) in a corneal flap bed; and transmit the pulsed laser beam in the second portion of the sub-surface region with the second scan pattern, wherein the second scan pattern comprises scanning the pulsed laser beam in a raster pattern.

14. The system of claim 13, wherein the region is a substantially circular region having a central portion, and wherein the second portion comprises the central portion.

15. The system of claim 13, wherein the controller is further configured to select a compound pattern comprising the first scan pattern and the second scan pattern.

16. The system of claim 13, wherein the pulsed laser beam has a pulse frequency selected from a range of about 1 kHz to about 1 GHz.

17. The system of claim 13, wherein the first pulse energy is less than or equal to about 800 nanoJoules.

18. The system of claim 13, wherein the controller is further configured to control movement of the scanner and direct the pulsed laser beam to create a side cut around a desired perimeter of the corneal flap while leaving an uncut segment to serve as a hinge for the flap, and wherein transmission of the pulsed laser beam in the first and second scan patterns forms a resection bed the perimeter of which is approximately defined by and slightly greater than the side cut.

* * * * *